(12) United States Patent
Ohara et al.

(10) Patent No.: US 6,809,114 B2
(45) Date of Patent: Oct. 26, 2004

(54) 4-AMINOBENZOPYRAN DERIVATIVES

(75) Inventors: Yoshio Ohara, Funabashi (JP);
Kazuhiko Ohrai, Funabashi (JP);
Kazufumi Yanagihara, Funabashi (JP);
Yukihiro Shigeta, Funabashi (JP); Toru Tsukagoshi, Funabashi (JP); Toru Yamashita, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/466,175

(22) PCT Filed: Feb. 14, 2002

(86) PCT No.: PCT/JP02/01236
§ 371 (c)(1),
(2), (4) Date: Jul. 14, 2003

(87) PCT Pub. No.: WO02/064581
PCT Pub. Date: Aug. 22, 2002

(65) Prior Publication Data
US 2004/0068002 A1 Apr. 8, 2004

(30) Foreign Application Priority Data
Feb. 14, 2001 (JP) ........................................ 2001-036293

(51) Int. Cl.⁷ ............................................ A61K 31/335
(52) U.S. Cl. ........................ 514/456; 549/399; 549/404
(58) Field of Search ........................ 514/456; 549/399, 549/404

(56) References Cited

U.S. PATENT DOCUMENTS 6,555,574 B1 * 4/2003 Tanikawa et al. ........... 514/456
6,589,983 B1 * 7/2003 Tanikawa et al. ........... 514/456
6,677,371 B1 * 1/2004 Tanikawa et al. ........... 514/456

OTHER PUBLICATIONS

John M. Evans et al.; "Synthesis and Antihypertensive Activity of 6,7–Disubstituted trans–4–Amino–3,4–dihydro–2,2–dimethyl–2H–1–benzopyran–3–ols"; J. Med. Chem.; 1984; pp 1127–1131.

Valerie A. Ashwood et al.; Synthesis and Antihypertensive Activity of 4–(Cyclic amido)–2H–1–benzopyrans; J. Med. Chem.; 1986; pp 2194–2201.

Jeffrey T. North et al.; Synthesis of 6–Cyano–2, 2–dimethyl–2H–1–benzopyran and Other Substituted 2,2–Dimethyl–2H–1–benzopyrans; J. Org. Chem.; 1995; pp 3397–3400.

* cited by examiner

Primary Examiner—Amelia A. Owens
(74) Attorney, Agent, or Firm—Oliff & Berridge, PLC

(57) ABSTRACT

This invention relates to benzopyran derivatives of the formula (I) wherein, $R^1$ and $R^2$ represent each independently a $C_{1-6}$alkyl group, etc, $R^3$ represents a hydroxyl group, etc, $R^4$ represents a hydrogen atom, etc, $R^6$ represents a hydrogen atom, $R^7$ represents a hydrogen atom, etc, X is absent, or represents C=O, etc, $R^8$ represents a hydrogen atom, a $C_{1-6}$alkyl group, etc, $R^9$ represents a hydrogen atom or a nitro group, when $R^9$ represents a nitro group, Y represents a $C_{4-8}$alkylene group, —$(CH_2)_m$—$CR^{11}R^{12}$—$(CH_2)_n$— or —$(CH_2)_o$—O—$(CH_2)_p$—, $R^5$ represents a hydrogen atom, an amino group, a $C_{1-6}$alkoxy group, a $C_{1-6}$alkylthio group, a $C_{1-6}$alkylamino group, a $C_{1-6}$ alkoxycarbonylamino group, etc, or pharmaceutically acceptable salts thereof. These compounds are useful as an antiarrhythmic agent.

11 Claims, No Drawings

4-AMINOBENZOPYRAN DERIVATIVES

TECHNICAL FIELD

The present invention relates to benzopyran derivatives having a prolongation effect on the refractory period, which are used for treatments of arrhythmia in mammals including human being.

BACKGROUND ART

As benzopyran derivatives, there have been known 4-acylaminobenzopyran derivatives exemplified by Cromakalim (Japanese Patent Application Laid-Open No. Sho 58-67683). These 4-acylaminobenzopyran derivatives exemplified by Cromakalim are known to open an ATP sensitive $K^+$ channel and to be effective for treatments of hypertension and asthma, but there has not been any mention as to the treatment of arrhythmia based on a prolongation effect on the refractory period.

Now, conventional antiarrhythmic agents having a prolongation effect on the refractory period as a main function (such as Class I drugs of antiarrhythmic agent classification according to Vaughan Williams, or d-sotalol belonging to Class III) have highly dangerous arrhythmic inducing actions that can result in sudden death such as torsades de pointes based on extension of ventricular muscle action potential relating to the prolongation effect on the refractory period, which become the therapeutic problems. Thus, agents having less side effects are desired.

DISCLOSURE OF INVENTION

The inventors of the present invention have made an intensive search and study of compounds having a prolongation effect on the refractory period more selective for atrium muscle than for ventricular muscle, and found that the compound of the formula (I) has a prolongation effect on the refractory period selective for atrium muscle without any influence on the refractory period and action potential of ventricular muscle.

The inventors of the present invention have studied eagerly benzopyran derivatives, and surprisingly found that the compound of the formula (I) has a strong prolongation effect on the refractory period, and that it is useful as an antiarrhythmic agent. The present invention has been made based on this finding.

The present invention relates to a benzopyran derivative of the formula (I)

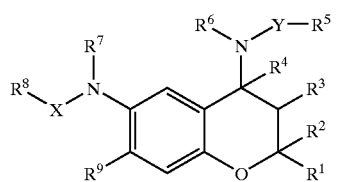

(I)

wherein, $R^1$ and $R^2$ represent each independently a hydrogen atom or a $C_{1-6}$alkyl group in which said alkyl group may be optionally substituted with a halogen atom, a hydroxyl group or a $C_{1-6}$alkoxy group in which said alkoxy group may be optionally substituted with a fluorine atom, $R^3$ represents a hydroxyl group or a $C_{1-6}$alkylcarbonyloxy group, $R^4$ represents a hydrogen atom, or $R^3$ and $R^4$ together form a bond, $R^6$ represents a hydrogen atom, $R^7$ represents a hydrogen atom or a $C_{1-6}$alkyl group, X is absent, or represents C=O or $SO_2$, $R^8$ represents a hydrogen atom or a $C_{1-6}$alkyl group in which said alkyl group may be optionally substituted with a hydroxyl group or a $C_{1-6}$alkoxy group, $R^9$ represents a hydrogen atom or a nitro group, when $R^9$ represents a hydrogen atom, Y represents a $C_{3-8}$alkylene group or —$(CH_2)_m$—$CR^{11}R^{12}$—$(CH_2)_n$— in which m and n represent each independently 0, 1, 2, 3 or 4, and m+n is equal to or more than 2; when m represents 0, $R^{11}$ and $R^{12}$ represent each independently a $C_{1-6}$alkyl group, and when m represents those other than 0, $R^{11}$ and $R^{12}$ represent each independently a $C_{1-3}$alkyl group or a hydroxyl group, or $R^{11}$ and $R^{12}$ together form a oxygen atom, $R^5$ represents a fluorine atom, a trifluoromethyl group, an amino group, a $C_{1-6}$alkylthio group, a $C_{1-6}$alkylamino group, a di-$C_{1-6}$alkylamino group, a $C_{1-6}$alkylcarbonylamino group, a $C_{1-6}$alkylsulfonylamino group, an aminocarbonyl group, a $C_{1-6}$alkylaminocarbonyl group, a di-$C_{1-6}$alkylaminocarbonyl group, a $C_{1-6}$alkylcarbonyl group, a $C_{1-6}$alkoxycarbonyl group, a $C_{1-6}$alkoxycarbonylamino group, an aminosulfonyl group, a $C_{1-6}$alkylsulfonyl group, a carboxyl group or a benzoyl group in which said benzoyl group may be optionally substituted with a $C_{1-6}$alkyl group, a $C_{1-6}$alkoxy group, a halogen atom, a nitro group or a cyano group, and when $R^9$ represents a nitro group, Y represents a $C_{4-8}$alkylene group, —$(CH_2)_m$—$CR^{11}R^{12}$—$(CH_2)_n$— in which m, n, $R^{11}$ and $R^{12}$ are same as the above or —$(CH_2)_o$—O—$(CH_2)_p$— in which o and p represent each independently 2, 3 or 4, $R^5$ represents a hydrogen atom, a fluorine atom, a trifluoromethyl group, a hydroxyl group, a formamide group, an amino group, a $C_{1-6}$alkoxy group, a $C_{3-8}$cycloalkyl group, a $C_{1-6}$alkylthio group, a $C_{1-6}$alkylamino group, a di-$C_{1-6}$alkylamino group, a $C_{1-6}$alkylcarbonylamino group, a $C_{1-6}$alkylsulfonylamino group, an aminocarbonyl group, a $C_{1-6}$alkylaminocarbonyl group, a di-$C_{1-6}$alkylaminocarbonyl group, a $C_{1-6}$alkylcarbonyl group, a $C_{1-6}$alkoxycarbonyl group, a $C_{1-6}$alkoxycarbonylamino group, an aminosulfonyl group, a $C_{1-6}$alkylsulfonyl group, a carboxyl group or a benzoyl group in which said benzoyl group may be optionally substituted with a $C_{1-6}$alkyl group, a $C_{1-6}$alkoxy group, a halogen atom, a nitro group or a cyano group;

or a pharmaceutically acceptable salt thereof.

The compound according to the present invention has a strong prolongation effect on the refractory period and it can be used as a drug for treating arrhythmia.

Respective substituents for the compound (I) according to the present invention are illustrated concretely specifically as follows.

Herein, "n" means normal, "i" means iso, "s" means secondary, "t" means tertiary, "c" means cyclo, and "p" means para.

As $C_{1-3}$alkyl groups, there may be mentioned methyl, ethyl, n-propyl, i-propyl and c-propyl, etc.

As $C_{1-6}$alkyl groups, there may be mentioned methyl, ethyl, n-propyl, i-propyl, c-propyl, n-butyl, i-butyl, s-butyl, t-butyl, c-butyl, 1-pentyl, 2-pentyl, 3-pentyl, i-pentyl, neopentyl, 2,2-dimethylpropyl, c-pentyl, 1-hexyl, 2-hexyl, 3-hexyl, 1-methyl-n-pentyl, 1,1,2-trimethyl-n-propyl, 1,2,2-trimethyl-n-propyl, 3,3-dimethyl-n-butyl and c-hexyl, etc. Preferably, there may be mentioned methyl, ethyl, n-propyl, i-propyl and n-butyl.

As halogen atoms, there may be mentioned a fluorine atom, a chlorine atom, a bromine atom and an iodine atom. Preferably, there may be mentioned a fluorine atom, a chlorine atom and a bromine atom.

As $C_{1-6}$alkoxy groups, there may be mentioned methoxy, ethoxy, n-propoxy, i-propoxy, n-butoxy, i-butoxy, s-butoxy, t-butoxy, 1-pentyloxy, 2-pentyloxy, 3-pentyloxy, i-pentyloxy, neopentyloxy, 2,2-dimethylpropoxy, 1-hexyloxy, 2-hexyloxy, 3-hexyloxy, 1-methyl-n-pentyloxy, 1,1,2-trimethyl-n-propoxy, 1,2,2-trimethyl-n-propoxy and 3,3-dimethyl-n-butoxy, etc. Preferably, there may be mentioned methoxy, ethoxy, n-propoxy and i-propoxy.

As $C_{4-8}$alkylene groups, there may be mentioned butylene, pentylene, hexylene, heptylene and octylene, etc. Preferably, there may be mentioned pentylene.

As $C_{3-8}$alkylene groups, there may be mentioned propylene in addition to the aforementioned $C_{4-8}$alkylene groups. Preferably, there may be mentioned pentylene.

As $C_{1-6}$alkylcarbonyloxy groups, there may be mentioned methylcarbonyloxy, ethylcarbonyloxy, n-propylcarbonyloxy, i-propylcarbonyloxy, n-butylcarbonyloxy, i-butylcarbonyloxy, s-butylcarbonyloxy, t-butylcarbonyloxy, 1-pentylcarbonyloxy, 2-pentylcarbonyloxy, 3-pentylcarbonyloxy, i-pentylcarbonyloxy, neopentylcarbonyloxy, t-pentylcarbonyloxy, 1-hexylcarbonyloxy, 2-hexylcarbonyloxy, 3-hexylcarbonyloxy, 1-methyl-n-pentylcarbonyloxy, 1,1,2-trimethyl-n-propylcarbonyloxy, 1,2,2-trimethyl-n-propylcarbonyloxy and 3,3-dimethyl-n-butylcarbonyloxy, etc. Preferably, there may be mentioned methylcarbonyloxy, ethylcarbonyloxy, n-propylcarbonyloxy, i-propylcarbonyloxy, n-butylcarbonyloxy and t-butylcarbonyloxy.

As $C_{3-8}$cycloalkyl groups, there may be mentioned c-propyl, c-butyl, c-pentyl, c-hexyl, c-heptyl and c-octyl, etc. Preferably, there may be mentioned c-propyl, c-butyl and c-hexyl.

As $C_{1-6}$alkylthio groups, there may be mentioned metylthio, ethylthio, n-propylthio, i-propylthio, c-propylthio, n-butylthio, i-butylthio, s-butylthio, t-butylthio, c-butylthio, 1-pentylthio, 2-pentylthio, 3-pentylthio, i-pentylthio, neopentylthio, t-pentylthio, c-pentylthio, 1-hexylthio, 2-hexylthio, 3-hexylthio, c-hexylthio, 1-methyl-n-pentylthio, 1,1,2-trimethyl-n-propylthio, 1,2,2-trimethyl-n-propylthio and 3,3-dimethyl-n-butylthio, etc. Preferably, there may be mentioned methylthio, ethylthio, n-propylthio, i-propylthio and n-butylthio.

As $C_{1-6}$alkylamino groups, there may be mentioned methylamino, ethylamino, n-propylamino, i-propylamino, c-propylamino, n-butylamino, i-butylamino, s-butylamino, t-butylamino, c-butylamino, 1-pentylamino, 2-pentylamino, 3-pentylamino, i-pentylamino, neopentylamino, t-pentylamino, c-pentylamino, 1-hexylamino, 2-hexylamino, 3-hexylamino, c-hexylamino, 1-methyl-n-pentylamino, 1,1,2-trimethyl-n-propylamino, 1,2,2-trimethyl-n-propylamino and 3,3-dimethyl-n-butylamino, etc. Preferably, there may be mentioned methylamino, ethylamino, n-propylamino, i-propylamino and n-butylamino.

As di-$C_{1-6}$alkylamino groups, there may be mentioned dimethylamino, diethylamino, di-n-propylamino, di-1-propylamino, di-c-propylamino, di-n-butylamino, di-i-butylamino, di-s-butylamino, di-t-butylamino, di-c-butylamino, di-1-pentylamino, di-2-pentylamino, di-3-pentylamino, di-i-pentylamino, di-neopentylamino, di-t-pentylamino, di-c-pentylamino, di-1-hexylamino, di-2-hexylamino, di-3-hexylamino, di-c-hexylamino, di-(1-methyl-n-pentyl)amino, di-(1,1,2-trimethyl-n-propyl)amino, di-(1,2,2-trimethyl-n-propyl)amino, di-(3,3-dimethyl-n-butyl)amino, methyl-(ethyl)amino, methyl(n-propyl)amino, methyl(i-propyl)amino, methyl(c-propyl)amino, methyl(n-butyl)amino, methyl(i-butyl)amino, methyl(s-butyl)amino, methyl(t-butyl)amino, methyl(c-butyl)amino, ethyl(n-propyl)amino, ethyl(i-propyl)amino, ethyl(c-propyl)amino, ethyl(n-butyl)amino, ethyl(i-butyl)amino, ethyl(s-butyl)amino, ethyl(t-butyl)amino, ethyl(c-butyl)amino, n-propyl(i-propyl)amino, n-propyl(c-propyl)amino, n-propyl(n-butyl)amino, n-propyl(i-butyl)amino, n-propyl(s-butyl)amino, n-propyl(t-butyl)amino, n-propyl(c-butyl)amino, i-propyl(c-propyl)amino, i-propyl(n-butyl)amino, i-propyl(i-butyl)amino, i-propyl(s-butyl)amino, i-propyl(t-butyl)amino, i-propyl(c-butyl)amino, c-propyl(n-butyl)amino, c-propyl(i-butyl)amino, c-propyl(s-butyl)amino, c-propyl(t-butyl)amino, c-propyl(c-butyl)amino, n-butyl(i-butyl)amino, n-butyl(s-butyl)amino, n-butyl(t-butyl)amino, n-butyl(c-butyl)amino, i-butyl(s-butyl)amino, i-butyl(t-butyl)amino, i-butyl(c-butyl)amino, s-butyl(t-butyl)amino, s-butyl(c-butyl)amino and t-butyl(c-butyl)amino, etc. Preferably, there may be mentioned dimethylamino, diethylamino, di-n-propylamino, di-i-propylamino and di-n-butylamino.

As $C_{1-6}$alkylcarbonylamino groups, there may be mentioned methylcarbonylamino, ethylcarbonylamino, n-propylcarbonylamino, i-propylcarbonylamino, n-butylcarbonylamino, i-butylcarbonylamino, s-butylcarbonylamino, t-butylcarbonylamino, 1-pentylcarbonylamino, 2-pentylcarbonylamino, 3-penylcarbonylamino, i-pentylcarbonylamino, neopentylcarbonylamino, t-pentylcarbonylamino, 1-hexylcarbonylamino, 2-hexylcarbonylamino and 3-hexylcarbonylamino, etc. Preferably, there may be mentioned methylcarbonylamino, ethylcarbonylamino, n-propylcarbonylamino, i-propylcarbonylamino and n-butylcarbonylamino.

As $C_{1-6}$alkylsulfonylamino groups, there may be mentioned methylsulfonylamino, ethylsulfonylamino, n-propylsulfonylamino, i-propyl-sulfonylamino, n-butylsulfonylamino, i-butylsulfonylamino, s-butylsulfonylamino, t-butylsulfonylamino, 1-pentylsulfonylamino, 2-pentylsulfonylamino, 3-pentylsulfonylamino, i-pentylsulfonylamino, neopentylsulfonylamino, t-pentylsulfonylamino, 1-hexylsulfonylamino, 2-hexylsulfonylamino and 3-hexylsulfonylamino, etc. Preferably, there may be mentioned methylsulfonylamino, ethylsulfonylamino, n-propylsulfonylamino, i-propylsulfonylamino and n-butylsulfonylamino.

As $C_{1-6}$alkylaminocarbonyl groups, there may be mentioned methylaminocarbonyl, ethylaminocarbonyl, n-propylaminocarbonyl, i-propylaminocarbonyl, n-butylaminocarbonyl, i-butylaminocarbonyl, s-butylaminocarbonyl, t-butylaminocarbonyl, 1-pentylaminocarbonyl, 2-pentylaminocarbonyl, 3-pentylaminocarbonyl, i-pentylaminocarbonyl, neopentylaminocarbonyl, t-pentylaminocarbonyl, 1-hexylaminocarbonyl, 2-hexylaminocarbonyl and 3-hexylaminocarbonyl, etc. Preferably, there may be mentioned methylaminocarbonyl, ethylaminocarbonyl, n-propylaminocarbonyl, i-propylaminocarbonyl and n-butylaminocarbonyl.

As di-$C_{1-6}$alkylaminocarbonyl groups, there may be mentioned dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-1-pentylaminocarbonyl, di-2-pentylaminocarbonyl, di-3-pentylaminocarbonyl, di-1-pentylaminocarbonyl, di-neopentylaminocarbonyl, di-t-pentylaminocarbonyl, di-c-pentylaminocarbonyl, di-1-hexylaminocarbonyl, di-2-hexylaminocarbonyl and di-3-hexylaminocarbonyl, etc. Preferably, there may be mentioned dimethylaminocarbonyl, diethylaminocarbonyl, di-n-propylaminocarbonyl, di-1-propylaminocarbonyl, di-c-propylaminocarbonyl and di-n-butylaminocarbonyl.

As $C_{1-6}$alkylcarbonyl groups, there may be mentioned methylcarbonyl, ethylcarbonyl, n-propylcarbonyl, i-propylcarbonyl, n-butylcarbonyl, i-butylcarbonyl, s-butylcarbonyl, t-butylcarbonyl, 1-pentylcarbonyl, 2-pentylcarbonyl, 3-pentylcarbonyl, i-pentylcarbonyl, neopentylcarbonyl, t-pentylcarbonyl, 1-hexylcarbonyl, 2-hexylcarbonyl and 3-hexylcarbonyl. Preferably, there may be mentioned methylcarbonyl, ethylcarbonyl, n-propylcarbonyl, i-propylcarbonyl and n-butylcarbonyl.

As $C_{1-6}$alkoxycarbonyl groups, there may be mentioned methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, 1-pentyloxycarbonyl, 2-pentyloxycarbonyl, 3-pentyloxycarbonyl, i-pentyloxycarbonyl, neopentyloxycarbonyl, t-pentyloxycarbonyl, 1-hexyloxycarbonyl, 2-hexyloxycarbonyl and 3-hexyloxycarbonyl, etc. Preferably, there may be mentioned methoxycarbonyl, ethoxycarbonyl, n-propoxycarbonyl, i-propoxycarbonyl, n-butoxycarbonyl, i-butoxycarbonyl, s-butoxycarbonyl and t-butoxycarbonyl.

As $C_{1-6}$alkoxycarbonylamino groups, there may be mentioned methoxycarbonylamino, ethoxycarbonylamino, n-propoxycarbonylamino, i-propoxycarbonylamino, n-butoxycarbonylamino, i-butoxycarbonylamino, s-butoxycarbonylamino, t-butoxycarbonylamino, 1-pentyloxycarbonylamino, 2-pentyloxycarbonylamino, 3-pentyloxycarbonylamino, i-pentyloxycarbonylamino, neopentyloxycarbonylamino, t-pentyloxycarbonylamino, 1-hexyloxycarbonylamino, 2-hexyloxycarbonylamino and 3-hexyloxycarbonylamino, etc. Preferably, there may be mentioned methoxycarbonylamino, ethoxycarbonylamino, n-propoxycarbonylamino, i-propoxycarbonylamino, n-butoxycarbonylamino, i-butoxycarbonylamino, s-butoxycarbonylamino and t-butoxycarbonylamino.

As $C_{1-6}$alkylsulfonyl groups, there may be mentioned methanesulfonyl and ethanesulfonyl.

As preferable compounds used in the present invention, the following compounds may be mentioned.

(1) The benzopyran derivative of the formula (I) or pharmaceutically acceptable salt thereof, wherein $R^1$ and $R^2$ represent a methyl group, $R^3$ represents a hydroxyl group and $R^4$ represents a hydrogen atom.

(2) The benzopyran derivative or pharmaceutically acceptable salt thereof according to aforementioned (1), wherein X represents C=O, $R^7$ represents a hydrogen atom, and $R^8$ represents a methyl group.

(3) The benzopyran derivative or pharmaceutically acceptable salt thereof according to aforementioned (1), wherein X is absent, and $R^7$ and $R^8$ represent a hydrogen atom.

(4) The benzopyran derivative or pharmaceutically acceptable salt thereof according to aforementioned (2), wherein $R^9$ represents a hydrogen atom.

(5) The benzopyran derivative or pharmaceutically acceptable salt thereof according to aforementioned (2), wherein $R^9$ represents a nitro group.

(6) The benzopyran derivative or pharmaceutically acceptable salt thereof according to aforementioned (3), wherein $R^9$ represents a hydrogen atom.

(7) The benzopyran derivative or pharmaceutically acceptable salt thereof according to aforementioned (3), wherein $R^9$ represents a nitro group.

Concrete examples of the compounds that can be used in the present invention are shown as follows, but the present invention is not limited thereto. Herein, "Me" means a methyl group, "Et" means an ethyl group, "Pr" means a propyl group, "Bu" means a butyl group, "Pen" means a pentyl group, "Hex" means a hexyl group, "Ac" means an acetyl group (COCH$_3$), "Ph" means a phenyl group, "n" means normal, "i" means iso, "t" means tertiary, and "c" means cyclo, respectively.

| $R^1$ | $R^2$ | Y | $R^5$ |
|---|---|---|---|
| H | H | (CH$_2$)$_3$ | NH$_2$ |
| Me | Me | (CH$_2$)$_5$ | NHMe |
| Me | Me | (CH$_2$)$_5$ | CO$_2$H |
| Me | Me | (CH$_2$)$_5$ | NMe$_2$ |
| Me | Me | (CH$_2$)$_6$ | COMe |
| Me | Me | (CH$_2$)$_3$ | CONH$_2$ |
| Me | Me | (CH$_2$)$_3$ | CO$_2$Et |
| Me | Me | (CH$_2$)$_4$ | CONHMe |
| Me | Me | (CH$_2$)$_5$ | NH$_2$ |
| Me | Me | (CH$_2$)$_6$ | NH$_2$ |
| Me | Me | (CH$_2$)$_4$ | COEt |
| Me | Me | (CH$_2$)$_4$ | CO$_2$Me |
| Me | Me | (CH$_2$)$_5$ | CO$_2$Me |
| Me | Me | (CH$_2$)$_4$CHOH(CH$_2$)$_2$ | COMe |
| Me | Me | (CH$_2$)$_4$ | NHMe |
| Me | Me | (CH$_2$)$_4$CHMeCH$_2$ | NH$_2$ |
| Me | Me | (CH$_2$)$_2$CMe$_2$(CH$_2$)$_2$ | NH$_2$ |
| Me | Me | (CH$_2$)$_5$ | CONH$_2$ |
| Et | Et | (CH$_2$)$_5$ | CONHMe |
| Et | Et | (CH$_2$)$_5$ | NHMe |
| n-Pr | n-Pr | (CH$_2$)$_5$ | NH$_2$ |
| i-Pr | i-Pr | (CH$_2$)$_5$ | NH$_2$ |
| n-Bu | n-Bu | (CH$_2$)$_5$ | NH$_2$ |
| i-Bu | i-Bu | (CH$_2$)$_5$ | CONH$_2$ |
| t-Bu | t-Bu | (CH$_2$)$_5$ | NHCOMe |
| n-Pen | n-Pen | (CH$_2$)$_5$ | NHCOMe |
| n-Hex | n-Hex | (CH$_2$)$_5$ | CONH$_2$ |
| CF$_3$ | CF$_3$ | (CH$_2$)$_5$ | NH$_2$ |
| CH$_2$OCH$_3$ | CH$_2$OCH$_3$ | (CH$_2$)$_5$ | NH$_2$ |

| $R^1$ | $R^2$ | $R^3$ | $R^7$ | X | $R^8$ |
|---|---|---|---|---|---|

-continued

| | | | | | |
|---|---|---|---|---|---|
| H | H | OH | H | — | H |
| Me | Me | OH | H | — | Me |
| Me | Me | OH | H | C=O | H |
| Me | Me | OH | H | C=O | Me |
| Me | Me | OH | H | C=O | Et |
| Me | Me | OH | H | C=O | n-Pr |
| Me | Me | OH | H | C=O | i-Pr |
| Me | Me | OH | H | C=O | n-Bu |
| Me | Me | OH | H | C=O | i-Bu |
| Me | Me | OH | H | C=O | t-Bu |
| Me | Me | OH | H | C=O | n-Pen |
| Me | Me | OH | H | C=O | n-Hex |
| Me | Me | OH | H | $SO_2$ | Me |
| Me | Me | OCOMe | H | $SO_2$ | c-Pen |
| Me | Me | OCOEt | H | C=O | c-Pr |
| Me | Me | OH | Me | — | c-Bu |
| Me | Me | OH | Et | — | $CH_2OCH_3$ |
| Me | Me | OH | n-Pr | — | c-Hex |
| Et | Et | OH | i-Pr | C=O | Me |
| Et | Et | OH | n-Bu | C=O | Me |
| n-Pr | n-Pr | OH | i-Bu | C=O | Me |
| i-Pr | i-Pr | OH | t-Bu | C=O | Me |
| n-Bu | n-Bu | OH | n-Pen | C=O | Me |
| i-Bu | i-Bu | OH | n-Hex | C=O | Me |
| t-Bu | t-Bu | OH | Me | C=O | Me |
| n-Pen | n-Pen | OH | H | C=O | Me |
| n-Hex | n-Hex | OH | H | C=O | Me |
| $CF_3$ | $CF_3$ | OH | H | C=O | Me |
| $CH_2OCH_3$ | $CH_2OCH_3$ | OH | H | C=O | Me |

| $R^1$ | $R^2$ | Y | $R^5$ |
|---|---|---|---|
| H | H | $(CH_2)_3$ | $NH_2$ |
| Me | Me | $(CH_2)_3O(CH_2)_2$ | NHMe |
| Me | Me | $(CH_2)_3O(CH_2)_2$ | $CO_2H$ |
| Me | Me | $(CH_2)_5$ | $NMe_2$ |
| Me | Me | $(CH_2)_6$ | COMe |
| Me | Me | $(CH_2)_3$ | $CONH_2$ |
| Me | Me | $(CH_2)_3$ | $CO_2Et$ |
| Me | Me | $(CH_2)_4$ | CONHMe |
| Me | Me | $(CH_2)_5$ | $NH_2$ |
| Me | Me | $(CH_2)_6$ | $NH_2$ |
| Me | Me | $(CH_2)_4$ | COEt |
| Me | Me | $(CH_2)_4$ | $CO_2Me$ |
| Me | Me | $(CH_2)_5$ | $CO_2Me$ |
| Me | Me | $(CH_2)_4CHOH(CH_2)_2$ | COMe |
| Me | Me | $(CH_2)_4$ | NHMe |
| Me | Me | $(CH_2)_4CHMeCH_2$ | $NH_2$ |
| Me | Me | $(CH_2)_2CMe_2(CH_2)_2$ | $NH_2$ |
| Me | Me | $(CH_2)_5$ | $CONH_2$ |
| Et | Et | $(CH_2)_5$ | CONHMe |
| Et | Et | $(CH_2)_5$ | NHMe |
| n-Pr | n-Pr | $(CH_2)_5$ | $NH_2$ |
| i-Pr | i-Pr | $(CH_2)_5$ | $NH_2$ |
| n-Bu | n-Bu | $(CH_2)_5$ | $NH_2$ |
| i-Bu | i-Bu | $(CH_2)_5$ | $CONH_2$ |
| t-Bu | t-Bu | $(CH_2)_5$ | NHCOMe |
| n-Pen | n-Pen | $(CH_2)_5$ | NHCOMe |
| n-Hex | n-Hex | $(CH_2)_5$ | $CONH_2$ |
| $CF_3$ | $CF_3$ | $(CH_2)_5$ | $NH_2$ |
| $CH_2OCH_3$ | $CH_2OCH_3$ | $(CH_2)_5$ | $NH_2$ |

-continued

| Y | $R^5$ |
|---|---|
| $(CH_2)_4$ | H |
| $(CH_2)_4$ | $NH_2$ |
| $(CH_2)_4$ | $NHSO_2Me$ |
| $(CH_2)_4$ | $NMe_2$ |
| $(CH_2)_4$ | $CONH_2$ |
| $(CH_2)_4$ | $CO_2Et$ |
| $(CH_2)_4$ | $CONMe_2$ |
| $(CH_2)_4$ | NHCOMe |
| $(CH_2)_5$ | H |
| $(CH_2)_5$ | $NHSO_2Me$ |
| $(CH_2)_5$ | NHMe |
| $(CH_2)_5$ | $CO_2Et$ |
| $(CH_2)_5$ | c-Hex |
| $(CH_2)_5$ | CONHMe |
| $(CH_2)_5$ | $CONMe_2$ |
| $(CH_2)_5$ | NHCOMe |
| $(CH_2)_6$ | H |
| $(CH_2)_6$ | COPh |
| $(CH_2)_6$ | NHMe |
| $(CH_2)_6$ | $NMe_2$ |
| $(CH_2)_6$ | $CONH_2$ |
| $(CH_2)_2O(CH_2)_2$ | H |
| $(CH_2)_3O(CH_2)_2$ | H |
| $(CH_2)_4O(CH_2)_2$ | H |
| $(CH_2)_3OCH_2$ | H |
| $(CH_2)_4C=OCH_2$ | H |
| $CHOHCH_2$ | H |
| $CH_2CHMeCH_2$ | H |
| $CH_2CMe_2CH_2$ | H |

| Y | $R^5$ |
|---|---|
| $(CH_2)_4$ | H |
| $(CH_2)_4$ | $NH_2$ |
| $(CH_2)_4$ | NHMe |
| $(CH_2)_4$ | $NMe_2$ |
| $(CH_2)_4$ | $CONH_2$ |
| $(CH_2)_4$ | CONHMe |
| $(CH_2)_4$ | $CONMe_2$ |
| $(CH_2)_4$ | NHCOMe |
| $(CH_2)_5$ | SMe |
| $(CH_2)_5$ | $NH_2$ |
| $(CH_2)_5$ | NHMe |
| $(CH_2)_5$ | $NMe_2$ |
| $(CH_2)_5$ | $CONH_2$ |
| $(CH_2)_5$ | CONHMe |
| $(CH_2)_5$ | $CONMe_2$ |
| $(CH_2)_5$ | NHCOMe |
| $(CH_2)_6$ | H |
| $(CH_2)_6$ | $NH_2$ |
| $(CH_2)_6$ | NHMe |
| $(CH_2)_6$ | $NMe_2$ |
| $(CH_2)_6$ | $CONH_2$ |
| $(CH_2)_2O(CH_2)_2$ | H |
| $(CH_2)_3O(CH_2)_2$ | H |
| $(CH_2)_4O(CH_2)_2$ | H |
| $(CH_2)_3OCH_2$ | H |

-continued

| | |
|---|---|
| $(CH_2)_4C=OCH_2$ | H |
| $CHOHCH_2$ | H |
| $CH_2CHMeCH_2$ | H |
| $CH_2CMe_2CH_2$ | H |

The compound according to the present invention has asymmetric carbon atoms at 3-position and 4-position, thus optical isomers thereof based on the asymmetric carbon atoms are present, which can be used in the application of the present invention similar to racemate. Further, a cis- and trans isomer based on configuration at 3-position and 4-position may be included, but the trans isomer is preferable.

Further, when the compounds can form their salts, the pharmaceutically acceptable salts thereof can be also used as active ingredients.

As pharmaceutically acceptable salts, there may be mentioned hydrochlorides, hydrobromides, sulfates, methanesulfonates, acetates, benzoates, tartrates, phosphates, lactates, maleates, fumarates, malates, gluconates and salicylates, etc. Preferably, there may be mentioned hydrochlorides, methanesulfonates and maleates.

Then, the preparation method of the compound according to the present invention is illustrated.

Of the compounds of the general formula (I), those wherein $R^4$ represents a hydrogen atom and $R^3$ represents a hydroxyl group, which are the compounds of formula (I-a), can be obtained by reacting a compound of the general formula (2) with a compound (3) in an inert solvent, as shown in the following reaction scheme.

The compound of the general formula (2) can be synthesized according to known methods (methods described in J. M. Evans et al., J. Med. Chem. 1984, 27, 1127; J. Med. Chem. 1986, 29, 2194; J. T. North et al., J. Org. Chem. 1995, 60, 3397; as well as Japanese Patent Application Laid-Open No. Sho 56-57785, Japanese Patent Application Laid-Open No. Sho 56-57786, Japanese Patent Application Laid-Open No. Sho 58-188880, Japanese Patent Application Laid-Open No. Hei 2-141, Japanese Patent Application Laid-Open No. Hei 10-87650 and Japanese Patent Application Laid-Open No. Hei 11-209366, etc.).

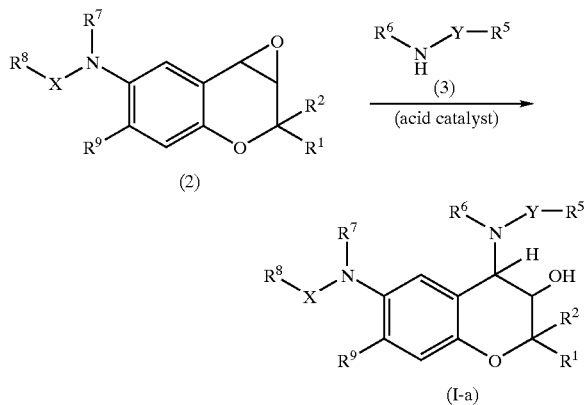

As the solvents used in the reaction of the compound of the general formula (2) with the compound (3), the following may be mentioned.

There may be mentioned sulfoxide type solvents exemplified by dimethylsulfoxide; amide type solvents exemplified by dimethylformamide and dimethylacetamide; ether type solvents exemplified by ethylether, dimethoxyethane and tetrahydrofuran; halogen type solvents exemplified by dichloromethane, chloroform and dichloroethane; nitrile type solvents exemplified by acetonitrile and propionitrile; aromatic hydrocarbon type solvents exemplified by benzene and toluene; hydrocarbon type solvents exemplified by hexane and heptane; and ester type solvents exemplified by ethyl acetate. Further, the reaction can be carried out in the absence of a solvent. Preferably, ether type solvents and nitrile type solvents may be mentioned.

The reaction temperature is generally from −80° C. to the reflux temperature of the reaction solvent, preferably from −10° C. to 100° C.

The molar ratio of the reaction materials is within the range of 0.5–20.0, preferably 1.0–10.0, for the compound (3)/the compound (2).

An acid catalyst may be used in the reaction.

As the acid catalysts used, there may be mentioned inorganic acids exemplified by hydrochloric acid and sulfuric acid, and Lewis acids exemplified by aluminum chloride, titanium tetrachloride, boron trifluoride diethyl ether complex, perchloric acid, lithium perchlorate, lithium bromide and ytterbium trifluoromethanesulfonate, etc. Preferably, there may be mentioned lithium bromide, perchloric acid and lithium perchlorate.

Of the compounds of the general formula (I), those other than the compounds of the formula (I-a) (the compounds wherein $R^3$ and $R^4$ together form a bond and the compounds wherein $R^4$ represents a hydrogen atom and $R^3$ represents a $C_{1-6}$ alkylcarbonyloxy group) can be prepared by the methods similar to those described in Japanese Patent Application Laid-Open No. Sho 52-91866 and Japanese Patent Application Laid-Open No. Hei 10-87650, etc.

Syntheses of optically active compounds of the compounds of the general formula (I) can be attained by utilizing optical resolution methods (Japanese Patent Application Laid-Open No. Hei 3-141286, U.S. Pat. No. 5,097,037 and European Patent No. 409,165). Further, syntheses of optically active compounds of the general formula (2) can be attained by utilizing asymmetric synthesis methods (Japanese National Publication No. Hei 5-507645, Japanese Patent Application Laid-Open No. Hei 5-301878, Japanese Patent Application Laid-Open No. Hei 7-285983, European Patent Application Laid-open No.535,377 and U.S. Pat. No. 5,420,314).

As described above, the inventors of the present invention found that the compound of the formula (I) has a strong prolongation effect on the refractory period. The prolongation effect on the refractory period is one of the functions of antiarrhythmic action and an important indicator that can be extrapolated to efficiency for clinical arrhythmia. Conventional antiarrhythmic agents having a prolongation effect on the refractory period as the main function (such as d-sotalol belonging to Class III of the antiarrhythmic agent classification according to Vaughan Williams) have highly dangerous arrhythmic inducing actions that can result in sudden death such as torsades de pointes based on extension of ventricular muscle action potential relating to the prolongation effect on the refractory period, which become the therapeutic problems for arrhythmia based on atrium (such as supraventricular tachycardia, atrial flutter and atrial fibrillation). In order to solve the problems, the inventors of the present invention carried out searching and studying of compounds having the prolongation effect on the refractory period more selective for atrium muscle than for ventricular muscle, and found that the compound of the formula (I) has the prolongation effect on the refractory period selective for atrium muscle without any influence on the refractory period and action potential of ventricular muscle. The difference between the findings by the inventors of the present invention and the known techniques is to provide the prolongation effect on the refractory period selective for atrium muscle to these compound group, which is shown by the following facts; there is no influence on the action potential sustaining period of removed ventricular muscle, and there is no influence on the electrocardiogram QT of anesthetized animal. From the above, the compounds of the present invention have no arrhythmic inducing action in ventricular muscle, thus they can provide possibilities of a contribution to more safe uses for arrhythmia based on atrium muscle than known techniques. This technique is useful for therapeutic or preventive uses as anti-atrial fibrillation agents, anti-atrial flutter agents and anti-atrial tachycardia agents relating to paroxysmal, chronic, preoperative, intraoperative or postoperative atrial arrhythmia, prevention of proceeding to embolus based on atrial arrhythmia, prevention of proceeding to ventricular arrhythmia or tachycardia originated from atrial arrhythmia or tachycardia, and prevention of the life prognosis worsening based on the preventive action for atrial arrhythmia or tachycardia which can be proceeded to ventricular arrhythmia or tachycardia.

The present invention provides a pharmaceutical composition or veterinary pharmaceutical composition containing a compound of the generally formula (I) in an effective amount for these treatments.

As administering forms of the compound according to the present invention, there may be mentioned parenteral administrations by means of injections (subcutaneous, intravenous, intramuscular and intraperitoneal injections), ointments, suppositories and aerosol, and oral administrations by means of tablets, capsules, granules, pills, syrups, solutions, emulsions and suspensions, etc.

The aforementioned pharmaceutical or veterinary pharmaceutical composition contains the compound according to the present invention in an amount of about 0.01–99.5%, preferably about 0.1–30%, of the total composition weight. In addition to the compound according to the present invention or the composition containing the compound, other pharmaceutically or veterinary pharmaceutically active compounds may be contained. Further, these compositions may contain the plurality of compounds according to the present invention.

A clinical administration amount of the compound of the present invention varies depending on age, weight and sensitivity of the patient, extent of condition, etc. and an effective administration amount is generally about 0.003–1.5 g, preferably 0.01–0.6 g, per day for adult. If necessary, however, the amount outside of the aforementioned range may be used.

The compound according to the present invention is formulated for administration by conventional pharmaceutical means.

That is, tablets, capsules, granules and pills for oral administration are prepared by using excipients such as sucrose, lactose, glucose, starch and mannitol; binders such as hydroxypropyl cellulose, syrup, gum arabic, gelatin, sorbitol, tragacanth, methyl cellulose and polyvinyl pyrrolidone; disintegrators such as starch, carboxymethyl cellulose or its calcium salt, microcrystalline cellulose and polyethylene glycol; lubricants such as talc, magnesium or calcium stearate, and silica; lubricaing agents such as sodium laurate and glycerol, etc.

Injections, solutions, emulsions, suspensions, syrups and aerosols are prepared by using solvents for the active components such as water, ethyl alcohol, isopropyl alcohol, propylene glycol, 1,3-butylene glycol and polyethylene glycol; surfactants such as sorbitan fatty acid ester, polyoxyethylene sorbitan fatty acid ester, polyoxyethylene fatty acid ester, polyoxyethylene ether of hydrogenated castor oil and lecithin; suspending agents such as carboxymethyl sodium salt, cellulose derivatives such as methyl cellulose, tragacanth, and natural rubbers such as gum arabic; and preserves such as p-hydroxybenzoic acid esters, benzalkonium chloride and sorbic acid salts, etc.

For ointments that are transdermally adsorptive pharmaceutics, for example, white vaseline, liquid paraffin, higher alcohols, Macrogol ointments, hydrophilic ointments and aqueous gel-type bases, etc are used.

Suppositories are prepared by using, for example, cocoa fats, polyethylene glycol, lanolin, fatty acid triglyceride, coconut oil and Polysorbate etc.

BEST MODE FOR CARRYING OUT THE INVENTION

The present invention is illustrated in detail by the Examples as follows, but the present invention is not limited to these Examples.

Herein, in following formulae, "Boc" means a t-butoxycarbonyl group.

SYNTHESIS EXAMPLES

Synthesis Example 1

(3R*,4S*)-6-acetylamino-3,4-dihydro-2,2-dimethyl-7-nitro-4-n-pentylamino-2H-1-benzopyran-3-ol

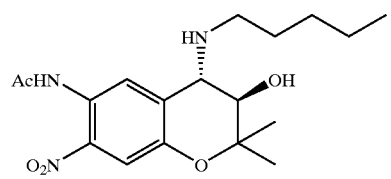

To a solution of 1.0 g (3.59 mmol) of (+)-(3R*,4R)-6-acetamide-3,4-epoxy-3,4-dihydro-2,2-dimethyl-7-nitro-2H-1-benzopyran (above 99% ee) and lithium perchlorate (1.53 g, 14.36 mmol) in acetonitrile (10 mL), n-pentylamine (0.942 mL, 7.18 mmol) was added at the room temperature and stirred at 65° C. for 3 hours. After an addition of an aqueous saturated sodium bicarbonate solution and an extraction with ethyl acetate, it was washed with an aqueous saturated sodium chloride solution and dried over anhydrous magnesium sulfate. A purification by silica gel column chromatography (Hex/AcOEt=1/2) was conducted to obtain the intended substance at 60% yield.

Yellow amorphous substance.

$^1$H-NMR (CDCl$_3$) δ: 0.89 (t, J=7.0 Hz, 3H), 1.22 (s, 3H), 1.30–1.36 (m, 4H), 1.52 (s, 3H), 1.48–1.56 (m, 2H), 2.55–2.71 (m, 2H), 3.57 (d, J=10.1 Hz, 1H), 3.70 (d, J=10.1 Hz, 1H), 7.62 (s, 1H), 8.68 (s, 1H), 10.02 (s, 1H).

MS (EI) m/z; 365 [M]$^+$, 308, 293 (bp).

The following compounds were obtained by the similar manner (Synthesis Examples 2–7).

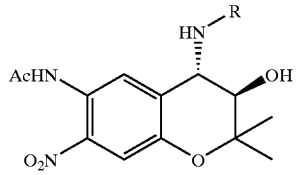

| Synthesis Example No. | R |
|---|---|
| 2 | HN~~~O~ |
| 3 | HN~~~S~ |
| 4 | HN~~~~ |
| 5 | HN~C(CH3)3 |
| 6 | HN~~-cyclohexyl |
| 7 | HN~~~~NHBoc |

Synthesis Example 2

56% yield.

Yellow amorphous substance.

$^1$H-NMR (CDCl$_3$) δ: 1.21 (s, 3H), 1.52 (s, 3H), 1.70 (s, 2H), 1.79 (quint, J=6.1 Hz, 2H), 2.26 (s, 3H), 2.70–2.85 (m, 2H), 3.36 (s, 3H), 3.54 (t, J=5.8 Hz, 2H), 3.58 (d, J=10.3 Hz, 1H), 3.71 (d, J=10.3 Hz, 1H), 7.62 (s, 1H), 8.68 (s, 1H), 10.00 (s, 1H).

MS (EI) m/z; 367 [M]$^+$, 297 (bp).

Synthesis Example 3

23% yield.

Yellow oil substance.

$^1$H-NMR (CDCl$_3$) δ: 1.22 (s, 3H), 1.53 (s, 3H), 1.62 (s, 2H), 1.83 (quint, J=6.8 Hz, 2H), 2.10 (s, 3H), 2.26 (s, 3H), 2.63 (t, J=7.0 Hz, 2H), 2.68–2.86 (m, 2H), 3.60 (d, J=10.2 Hz, 1H), 3.72 (d, J=10.2 Hz, 1H), 7.63 (s, 1H), 8.70 (s, 1H), 10.01 (s, 1H).

MS (EI) m/z; 383 [M]$^+$, 220 (bp).

Synthesis Example 4

93% yield.

Red oil substance.

$^1$H-NMR (CDCl$_3$) δ: 0.92 (t, J=7.2 Hz, 3H), 1.21 (s, 3H), 1.33–1.60 (m, 4H), 1.52 (s, 3H), 2.27 (s, 3H), 2.56–2.72 (m, 2H), 3.56 (d, J=10.2 Hz, 1H), 3.71 (d, J=10.2 Hz, 1H), 7.63 (s, 1H), 8.68 (s, 1H), 10.03 (s, 1H).

MS (EI) m/z; 353 [M]$^+$, 263, 222 (bp).

Synthesis Example 5

96% yield.

Red amorphous substance.

$^1$H-NMR (CDCl$_3$) δ: 0.89 (s, 9H), 1.21 (s, 3H), 1.46 (t, J=8.1 Hz, 2H), 1.53 (s, 3H), 2.27 (s, 3H), 2.53–2.72 (m, 2H), 3.69 (d, J=10.2 Hz, 1H), 3.71 (d, J=10.2 Hz, 1H), 7.63 (s, 1H), 8.68 (s, 1H), 10.02 (s, 1H).

MS (EI) m/z; 379 [M]$^+$, 260, 146 (bp).

Synthesis Example 6

89% yield.

Yellow crystal.

m.p. 210.0–212.0° C.

$^1$H-NMR (CDCl$_3$) δ: 0.85–1.90 (m, 13H), 1.18 (s, 3H), 1.54 (s, 3H), 2.25 (s, 3H), 2.76–2.85 (m, 1H), 3.08–3.18 (m, 1H), 4.05 (d, J=8.8 Hz, 1H), 4.59 (d, J=8.8 Hz, 1H), 7.68 (s, 1H), 8.78 (s, 1H), 9.77 (s, 1H).

MS (EI) m/z; 405 [M]$^+$, 335, 292 (bp).

Synthesis Example 7

98% yield.

Red oil substance.

$^1$H-NMR (CDCl$_3$) δ: 1.21 (s, 3H), 1.44 (s, 9H), 1.52 (s, 3H), 1.52–1.61 (m, 2H), 1.63–1.74 (m, 2H), 2.27 (s, 3H), 2.58–2.71 (m, 2H), 3.07–3.16 (m, 2H), 3.60 (d, J=10.1 Hz, 1H), 3.73 (d, J=10.1 Hz, 1H), 7.63 (s, 1H), 8.68 (s, 1H), 10.00 (s, 1H).

MS (EI) m/z; 466 [M]$^+$, 394, 277, 70 (bp).

Synthesis Example 8

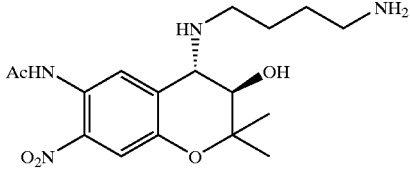

To the compound of Synthesis Example 7 (500 mg, 1.18 mmol), a hydrogen chloride-dioxane (4 mol/L) solution (1.18 mL, 4.72 mmol) was added under an ice cooling, stirred for 30 minutes, then heated to room temperature, and stirred for another 30 minutes. An aqueous sodium hydroxide (1 mol/L) was added thereto, an extraction was conducted with chloroform, an organic phase was washed once with an aqueous saturated sodium chloride solution and dried over anhydrous magnesium sulfate. A solvent was distilled off to obtain the intended substance at 100% yield.

Yellow solid.

$^1$H-NMR (CDCl$_3$) δ: 1.19 (s, 3H), 1.50 (s, 3H), 1.55–1.67 (m, 4H), 2.26 (s, 3H), 2.58–2.70 (m, 2H), 3.14 (brs, 4H), 3.64 (d, J=10.2 Hz, 1H), 3.75 (d, J=10.2 Hz, 1H), 7.61 (s, 1H), 8.65 (s, 1H), 10.02 (s, 1H).

MS (EI) m/z; 394 [M]$^+$, 350 (bp).

Synthesis Example 9

Trans-6-amino-3,4-dihydro-2,2-dimethyl-7-nitro-4-n-pentylamino-2H-1-benzopyran-3-ol

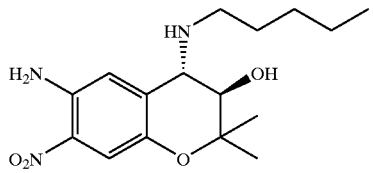

To the ethanol solution (11 mL) of compound of Synthesis Example 1 (550 mg, 1.51 mmol), a 35% hydrochloric acid (1.1 mL) was added at room temperature, and refluxed for 12 hours. An aqueous saturated sodium bicarbonate solution was added thereto, an extraction was conducted with ethyl acetate, an organic phase was washed once with an aqueous saturated sodium chloride solution and dried over anhydrous magnesium sulfate. After distilling off the solvent, the residue was purified by silica gel column chromatography (Hex/AcOEt=1/1) to obtain the intended substance at 75% yield.

Red amorphous substance.

$^1$H-NMR (CDCl$_3$) δ: 0.91 (t, J=8.1 Hz, 3H), 1.19 (s, 3H), 1.25–1.35 (m, 4H), 1.34 (s, 3H), 1.50–1.80 (m, 4H), 2.48–2.75 (m, 2H), 3.58–3.65 (m, 2H), 5.70 (s, 2H), 6.81 (s, 1H), 7.59 (s, 1H).

MS (EI) m/z; 323 [M]$^+$, 252 (bp).

PREPARATION EXAMPLES

Preparation Example 1

Tablet:

| | |
|---|---:|
| a compound according to the invention | 10 g |
| lactose | 260 g |
| microcrystalline cellulose | 600 g |
| corn starch | 350 g |
| hydroxypropyl cellulose | 100 g |
| CMC-Ca | 150 g |
| magnesium stearate | 30 g |
| total | 1,500 g |

The aforementioned ingredients were mixed by a conventional method and thereafter 10,000 sugar-coated tablets each containing 1 mg of the active ingredient per a tablet were prepared.

Preparation Example 2

Capsule:

| | |
|---|---:|
| a compound according to the invention | 10 g |
| lactose | 440 g |
| microcrystalline cellulose | 1,000 g |
| magnesium stearate | 50 g |
| total | 1,500 g |

The aforementioned ingredients were mixed by a conventional method and thereafter filled in gelatin capsules to prepare 10,000 capsules each containing 1 mg of the active ingredient per a capsule.

Preparation Example 3

Soft capsule:

| | |
|---|---:|
| a compound according to the invention | 10 g |
| PEG 400 | 479 g |
| saturated fatty acid triglyceride | 1,500 g |
| peppermint oil | 1 g |
| Polysorbate 80 | 10 g |
| total | 2,000 g |

The aforementioned ingredients were mixed by a conventional method and thereafter filled in No.3 soft gelatin capsules to prepare 10,000 soft capsules each containing 1 mg of the active ingredient per a capsule.

Preparation Example 4

Ointment:

| | |
|---|---:|
| a compound according to the invention | 1.0 g |
| liquid paraffin | 10.0 g |
| cetanol | 20.0 g |
| white vaseline | 68.4 g |
| ethylparaben | 0.1 g |
| l-menthol | 0.5 g |
| total | 100.0 g |

The aforementioned ingredients were mixed by a conventional method to obtain 1% ointment.

Preparation Example 5

Suppository:

| | |
|---|---:|
| a compound according to the invention | 1 g |
| Witepsol H15* | 478 g |
| Witepsol W35* | 520 g |
| Polysorbate 80 | 1 g |
| total | 1,000 g |

(*trade name of triglyceride type compounds)

The aforementioned ingredients were melt-mixed by a conventional method, poured into suppository containers and cooled to solidify, thereby 1,000 suppositories (1 g) each containing 1 mg of the active ingredient per a suppository were prepared.

Preparation Example 6

Injection:

| | |
|---|---:|
| a compound according to the invention | 1 mg |
| distilled water for injection | 5 mL |

It is used by dissolving when applied.

PHARMACOLOGICAL TEST EXAMPLE

Effects on the Effective Refractory Period

Method

Beagles were anesthetized with pentobarbital sodium and, under artificially ventilated condition, thoracotomy was conducted along the median and the pericardium was cut open to expose the heart. ECG was recorded using bipolar electrodes attached to the surface of the right atrial free wall, right atrial auricle, and right ventricular free wall. The vagal nerves were stimulated using an electric stimulation device via Nichrome wires inserted into the bilateral vagal nerves in the neck. The conditions for electric stimulation to the vagal nerves were set such that the RR intervals on ECG were prolonged by about 100 msec compared with those before the stimulation was started.

Electric current twice as strong as the threshold was used for the electric stimulation to the heart, and premature stimulation S2 was applied after giving 10 serial S1 stimulations at the basic stimulation cyclelength. To determine the effective refractory period, the S1–S2 interval was reduced by 2 msec, and the effective refractory period was defined as the point at which responses to premature stimulation S2 were lost.

For evaluation of drug effects, the atrial and ventricular effective refractory periods were determined before drug administration, then each compound was administrated intravenously at the dose of 0.3 mg/kg, and the atrial and ventricular effective refractory periods were determined from 5 min after the administration.

The results were shown as prolongation time in the atrial and ventricular effective refractory periods, i.e. [effective refractory period after administration]–[effective refractory period before administration] (msec).

TABLE 1

| compound (Synthesis Example No.) | prolongation time in effective refractory period (msec) | |
|---|---|---|
| | Atrium | ventricle |
| 1 | 40 | 5 |
| 6 | 23 | 0 |
| 9 | 27 | 3 |

Results

The compounds of the present invention showed an prolongation effect on the effective refractory period selective for atrium.

Effects of the Invention

Compounds according to the present invention exhibit prolongation effect on the effective refractory period selective for atrium, thus can be used as an anti-atrial fibrillation agents and an supraventricular antiarrhythmic agent, and are useful as pharmaceuticals. Further, since compounds according to the present invention have small influence on ventricle, they can contribute to safe treatments of aforementioned arrhythmic conditions.

What is claimed is:

1. A benzopyran compound of the formula (I)

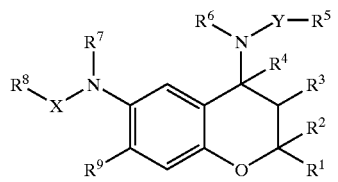

(I)

wherein, $R^1$ and $R^2$ represent each independently a hydrogen atom or a $C_{1-6}$alkyl group in which said alkyl group may be optionally substituted with a halogen atom, a hydroxyl group or a $C_{1-6}$alkoxy group in which said alkoxy group may be optionally substituted with a fluorine atom, $R^3$ represents a hydroxyl group or a $C_{1-6}$alkylcarbonyloxy group, $R^4$ represents a hydrogen atom, or $R^3$ and $R^4$ together form a bond, $R^6$ represents a hydrogen atom, $R^7$ represents a hydrogen atom or a $C_{1-6}$alkyl group, X is absent, or represents C=O or $SO_2$, $R^8$ represents a hydrogen atom or a $C_{1-6}$alkyl group in which said alkyl group may be optionally substituted with a hydroxyl group or a $C_{1-6}$alkoxy group, $R^9$ represents a hydrogen atom or a nitro group, when $R^9$ represents a hydrogen atom, Y represents a $C_{3-8}$alkylene group or —$(CH_2)_m$—$CR^{11}R^{12}$—$(CH_2)_n$— in which m and n represent each independently 0, 1, 2, 3 or 4, and m+n is equal to or more than 2; when m represents 0, $R^{11}$ and $R^{12}$ represent each independently a $C_{1-6}$alkyl group, and when m represents those other than 0, $R^{11}$ and $R^{12}$ represent each independently a $C_{1-3}$alkyl group or a hydroxyl group, or $R^{11}$ and $R^{12}$ together form a oxygen atom, $R^5$ represents a fluorine atom, a trifluoromethyl group, an amino group, a $C_{1-6}$alkylthio group, a $C_{1-6}$alkylamino group, a di-$C_{1-6}$alkylamino group, a $C_{1-6}$alkylcarbonylamino group, a $C_{1-6}$alkylsulfonylamino group, an aminocarbonyl group, a $C_{1-6}$alkylaminocarbonyl group, a di-$C_{1-6}$alkylaminocarbonyl group, a $C_{1-6}$alkylcarbonyl group, a $C_{1-6}$alkoxycarbonyl group, a $C_{1-6}$alkoxycarbonylamino group, an aminosulfonyl group, a $C_{1-6}$alkylsulfonyl group, a carboxyl group or a beuzoyl group in which said benzoyl group may be optionally substituted with a $C_{1-6}$alkyl group, a $C_{1-6}$alkoxy group, a halogen atom, a nitro group or a cyano group, and when $R^9$ represents a nitro group, Y represents a $C_{4-8}$alkylene group, —$(CH_2)_m$—$CR^{11}R^{12}$—$(CH_2)_n$— in which m, n, $R^{11}$ and $R^{12}$ are same as the above or —$(CH_2)_o$—O—$(CH_2)_p$— in which o and p represent each independently 2, 3 or 4, $R^5$ represents a hydrogen atom, a fluorine atom, a trifluoromethyl group, a hydroxyl group, a formamide group, an amino group, a $C_{1-6}$alkoxy group, a $C_{3-8}$cycloalkyl group, a $C_{1-6}$alkylthio group, a $C_{1-6}$alkylamino group, a di-$C_{1-6}$alkylamino group, a $C_{1-6}$alkylcarbonylamino group, a $C_{1-6}$alkylsulfonylamino group, an aminocarbonyl group, a $C_{1-6}$alkylaminocarbonyl group, a di-$C_{1-6}$alkylaminocarbonyl group, a $C_{1-6}$alkylcarbonyl group, a $C_{1-6}$alkoxycarbonyl group, a $C_{1-6}$alkoxycarbonylamino group, an aminosulfonyl group, a $C_{1-6}$alkylsulfonyl group, a carboxyl group or a benzoyl group in which said benzoyl group may be optionally substituted with a $C_{1-6}$alkyl group, a $C_{1-6}$alkoxy group, a halogen atom, a nitro group or a cyano group;

or a pharmaceutically acceptable salt thereof.

2. The benzopyran compound or pharmaceutically acceptable salt thereof according to claim 1, wherein $R^1$ and $R^2$ represent a methyl group, $R^3$ represents a hydroxyl group and $R^4$ represents a hydrogen atom.

3. The benzopyran compound or pharmaceutically acceptable salt thereof according to claim 2, wherein X represents C=O, $R^7$ represents a hydrogen atom, and $R^8$ represents a methyl group.

4. The benzopyran compound or pharmaceutically acceptable salt thereof according to claim 2, wherein X is absent, and $R^7$ and $R^8$ represent a hydrogen atom.

5. The benzopyran compound or pharmaceutically acceptable salt thereof according to claim 3, wherein $R^9$ represents a hydrogen atom.

6. The benzopyran compound or pharmaceutically acceptable salt thereof according to claim 3, wherein $R^9$ represents a nitro group.

7. The benzopyran compound or pharmaceutically acceptable salt thereof according to claim 4, wherein $R^9$ represents a hydrogen atom.

8. The benzopyran compound or pharmaceutically acceptable salt thereof according to claim 4, wherein $R^9$ represents a nitro group.

9. A pharmaceutical composition characterized by comprising a benzopyran compound or pharmaceutically acceptable salt thereof according to claim 1 as an active ingredient.

10. A pharmaceutical composition comprising a benzopyran compound or pharmaceutically acceptable salt thereof according to claim 1 as an active ingredient, wherein carbon atoms at a 3-position and at a 4-position are in a trans isomer configuration.

11. A method for treating arrhythmia, which comprises administering an effective amount of the benzopyran compound or pharmaceutically acceptable salt thereof of claim 1.

* * * * *